United States Patent [19]

Holick

[11] 4,424,161
[45] Jan. 3, 1984

[54] [1β³H] 1α,25 DIHYDROXYVITAMIN D₃ AND METHOD FOR ITS PREPARATION

[75] Inventor: Michael F. Holick, Sudbury, Mass.

[73] Assignee: Massachusetts General Hospital, Boston, Mass.

[21] Appl. No.: 101,525

[22] Filed: Dec. 10, 1979

[51] Int. Cl.³ .............................................. C09J 9/00
[52] U.S. Cl. .............................................. 260/397.2
[58] Field of Search .................................... 260/397.2

[56] References Cited

U.S. PATENT DOCUMENTS 4,022,768  5/1977  Matsunaga et al. ............ 260/397.2
4,119,647  10/1978  Liebman ........................ 260/397.2

Primary Examiner—Elbert L. Roberts
Attorney, Agent, or Firm—Oblon, Fisher, Spivak, McClelland & Maier

[57] ABSTRACT

[1β-³H] 1α,25 dihydroxyvitamin D₃ of high specific activity as well as a method for its preparation, which comprises reducing 1-keto 25(OH) previtamin D₃ with ³H-NaBH₄, separating the [1β-³H] 1α,25 dihydroxyprevitamin D₃ obtained therefrom from [1α-³H] 1β,25 25 dihydroxyprevitamin D₃ also present in the reaction mixture, and thermally equilibrating the separated [1β-³H] 1α,25 dihydroxyprevitamin D₃ with its [1β-³H] 1α,25-dihydroxyvitamin D₃ isomer.

The tritiated vitamin D₃ derivative is useful for metabolic, tracer and radioimmunoassay studies.

9 Claims, 2 Drawing Figures

[1β³H] 1α,25 DIHYDROXYVITAMIN $D_3$ AND METHOD FOR ITS PREPARATION

BACKGROUND OF THE INVENTION

1. Field of the Invention

The present invention relates to metabolically useful radioactive [$^3$H-1β]-1α,25 dihydroxyvitamin $D_3$ and to a method for its preparation.

2. Description of the Prior Art

Vitamin $D_3$ and its metabolites comprise one of the three important blood-calcium regulatory systems in the human body. The others are calcitonin and parathyroid hormone. Vitamin $D_3$ and two of its most important metabolites are shown (with standard numbering and ring-lettering system) in formulae Ia–c below:

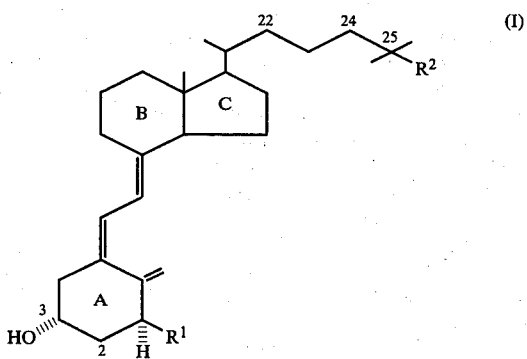

I(a) $D_3$: $R^1=R^2=H$;
I(b) 25-(OH)-$D_3$: $R_1=H$, $R^2=OH$;
I(c) 1α,25(OH)$_2$$D_3$: $R^1=R^2=OH$

Nutritional deficiency of Vitamin D or disturbances in the metabolism of the vitamin, cause such diseases as rickets, renal osteodystrophy and related bone diseases, as well as, generally, hypo- and hyper-calcemic states. The vitamin is therefore crucial in maintaining normal development of bone structure by regulating blood calcium levels.

Vitamin $D_3$ (Ia) is rapidly converted to 25-OH-$D_3$ (Ib) in the liver. In response to hypocalcemia, 25-OH-$D_3$, the major circulating metabolite of the vitamin, undergoes further metabolism in the kidney to 1α,25-(OH)$_2$-$D_3$ (Ic). 1α,25-(OH)$_2$-$D_3$ acts more rapidly than either $D_3$ or 25-OH-$D_3$. Additionally, 1α,25-(OH)$_2$-$D_3$ is 5-10 times more potent than $D_3$ and about 2-5 times more potent than 25-OH-$D_3$ in vivo, provided it is dosed parenterally and daily (Napoli, J. L. and DeLuca, H. F., "Blood Calcium Regulators" and references cited therein, in Burger's Medicinal Chemistry, 4th Edition Part II, Edited by Manfred Wolf, Wiley-Interscience, (1979), pp 725–739).

The ubiquitous role of 1α,25-(OH)$_2$$D_3$ in calcium metabolism, such as in the induction and formation of calcium binding proteins and responsibility for calcium transport and mobilization in the body, requires efficient and accurate clinical assays therefor, such as for example radioimmunoassays (RIA). For such radioimmunoassays, it is necessary to use radioactive 1α,25-(OH)$_2$-$D_3$, of high specific activity.

Other applications for radioactive 1α,25-(OH)$_2$-$D_3$—especially [1β-$^3$H]-1α,25(OH)$_2$-$D_3$—involve its use in metabolism and tracer studies and in competitive protein binding assays.

[1β-$^3$H]-1α,25(OH)$_2$-$D_3$ however, has not been described or disclosed to date and neither has a method been described for its preparation. Although methods for the stereospecific synthesis of non-radioactive 1α,2-5(OH)$_2$$D_3$ have been described, there existed prior to this invention no direct route to prepare the radioactive analogue, especially in high specific radioactivity.

The non-radiochemical transformations of 1α,2-5(OH)$_2$$D_3$ have been described by Paaren et al (J. Chem. Soc., Chem. Comm., p 396 (1977)). Sheves et al (J. Org. Chem., 42, 3597 (1977)) has been described the non-radiochemical transformation of 1α-hydroxyvitamin $D_3$ to 1β-hydroxyvitamin $D_3$. Paaren et al oxidized 1α,25(OH)$_2$$D_3$ with $MnO_2$ to the corresponding 1-keto25(OH) previtamin $D_3$ and subsequently reduced this 1-keto25(OH) previtamin $D_3$ with $LiAlH_4$ to a mixture of about 25% 1α,25(OH)$_2$ previtamin $D_3$ and about 75% 1β,25(OH)$_2$ previtamin $D_3$ which were separated by chromatography. Thermal isomerization of 1α,25(OH)$_2$ previtamin $D_3$ led to a mixture of 1α,2-5(OH)$_2$ previtamin $D_3$ and 1a,25(OH)$_2$ vitamin $D_3$ which were separated by high-pressure liquid chromatography. Paaren et al in the same reference suggest that 1-keto25(OH) previtamin $D_3$ would be a useful synthetic precursor to ring A-modified radiolabelled derivatives. However, since available $^3$H-LiAlH$_4$ has a maximum specific activity of only 100 mCi/mmol (New England Nuclear) the maximum possible specific radioactivity of a resulting [1β-$^3$H]1α,25(OH)$_2$-$D_3$ would be too low for most RIA, metabolism or tracer studies applications. In this respect it would be preferable to use $^3$H-NaBH$_4$, which is readily available with about 100–600 times the specific activity of $^3$H-LiAlH$_4$ (commercial $^3$H-NaBH$_4$ is available with a specific activity of up to 80 Ci/mmol, New England Nuclear). Sheves et al, supra use non-radioactive NaBH$_4$ to reduce 1-keto-previtamin $D_3$, also prepared by MnO$_2$ oxidation of 1α(OH)$D_3$. Sheves et al however report that reduction with NaBH$_4$ unfortunately gives a single product, namely 1α-hydroxyprevitamin $D_3$, without any 1α-hydroxyprevitamin $D_3$. Thermal equilibration of 1β-hydroxyprevitamin $D_3$ gives 1β(OH)$D_3$, an epimer of the natural vitamin which is biologically inactive. 1β,25(OH)$_2$ is also biologically inactive. (Paaren et al, supra, Sheves et al, supra, Lawson et al, FEBS Letters, 80, 137 (1977)). The use of $^3$H-NaBH$_4$ to prepare [1β-$^3$H]1α,25(OH)$_2$$D_3$ would therefore appear to be precluded by these findings. Absent an efficient method of synthesis of course, radiolabelled [1β-$^3$H]1α,25(OH)$_2$$D_3$ of high specific activity is not available to the art.

A need therefore continues to exist for radiolabelled [1β-$^3$H]1α,25(OH)$_2$$D_3$, especially of high specific radioactivity. A need also continues to exist for a method of synthesis of [1β,$^3$H]1α,25(OH)$_2$$D_3$.

SUMMARY OF THE INVENTION

It is therefore an object of the invention to provide [1β-$^3$H]1α,25(OH)$_2$$D_3$.

Another object of the invention is to provide [1β-$^3$H]1α,25(OH)$_2$$D_3$ of high specific activity.

Still another object of the invention is to provide a method of preparing [1β-$^3$H]1α,25(OH)$_2$$D_3$. These and other objects of the invention which will hereinafter become more readily apparent can be attained by providing [1β-$^3$H]1α,25(OH)$_2$$D_3$ and a method for its preparation which comprises: reducing 1-keto-25(OH) previtamin $D_3$ with $^3$H-NaBH$_4$ thereby obtaining a mixture of [1β-$^3$H]1α,25 dihydroxyprevitamin $D_3$ and [1α-

$^3H]1\beta,25$ dihydroxyprevitamin $D_3$ epimers, separating said [1B-$^3$H]1α epimer from said [1α-$^3$H]1B epimer, and thermally equilibrating said [1B-$^3$H]1α,25(OH)$_2$D$_3$ isomer.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DETAILED DESCRIPTION OF THE PREFERRED EMBODIMENTS

Figure 1:
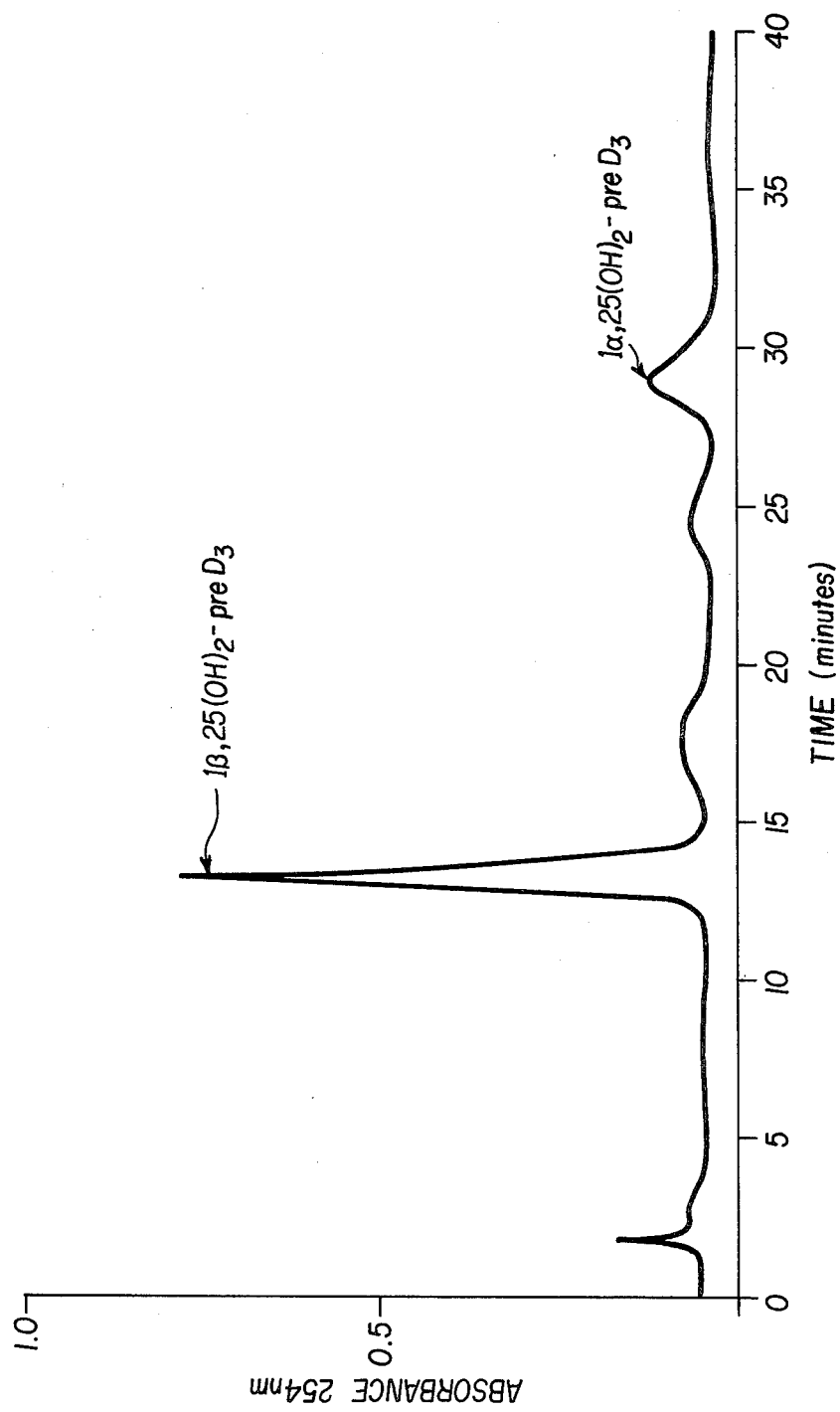
FIG. 1 is a high-pressure liquid chromatography profile of a mixture of 1α,25(OH)$_2$ previtamin D$_3$ and 1β,25(OH)$_2$ previtamin D$_3$ separated according to Example 1.

The present inventor has now discovered that reduction of 1-keto25(OH) previtamin D$_3$ (II, below) (prepared by MnO$_2$ oxidation of 1α,25(OH)$_2$D$_3$ or 1α,2-,5(OH)$_2$ previtamin D$_3$), with NaBH$_4$ or $^3$H-NaBH$_4$ yields a mixture of both 1α and 1β epimers of the 1,25 dihydroxy previtamin D$_3$ derivative (IIIa and IIIb respectively, eq.1):

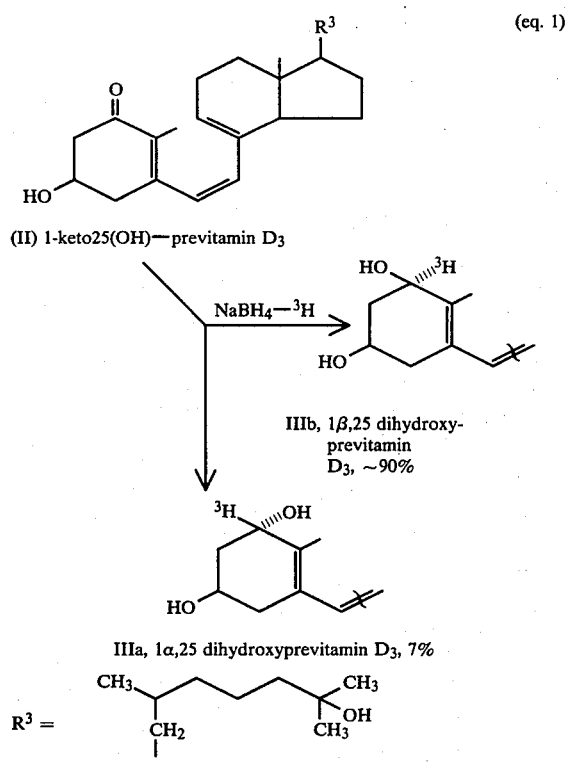

This observation directly contradicts the teachings of Sheves et al, which indicated that when NaBH$_4$ reduction is used, only the 1β(OH) previtamin D$_3$ is obtained. Because of this observation it becomes possible for the first time, to obtain [1β-$^3$H]1α,25(OH)$_2$D$_3$ in high specific activity. Once the 1α,25(OH)$_2$ previtamin D$_3$ is separated from the 1β,25(OH)$_2$ previtamin D$_3$ epimer, the 1α,25(OH)$_2$ preD$_3$ epimer is thermally isomerized to yield a mixture of itself with 1α,25(OH)$_2$D$_3$, the desired final product (IV, eq 2):

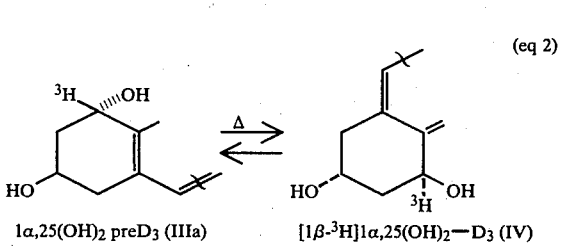

1α,25(OH)$_2$ preD$_3$ (IIIa)   [1β-$^3$H]1α,25(OH)$_2$—D$_3$ (IV)

Since $^3$H-NaBH$_4$ is available with specific activity of up to 80 Ci/mmol, the present synthetic route allows the preparation of [1β-$^3$H]1α,25(OH)$_2$D$_3$ of specific activity in the range 1–20 mM, preferably 5–20 Ci/mM. Obviously if $^3$H-NaBH$_4$ of higher specific activity becomes available, tritiated vitamin of even higher specific radioactivity can be prepared using the method of the present invention. The best available specific activity using $^3$H-LiAlH$_4$ would be 0.1 Ci/mM.

The preparation of 1 keto-25(OH) previtamin D$_3$ by MnO$_2$ oxidation of 1α,25(OH)$_2$ D$_3$ is well known and can be carried out following the teachings of Sheves et al (J. Org. Chem., 42, 3597 (1977)) or Paaren, H. E. et al (J. Chem. Soc., Chem. Comm. 1977, p 896). Any other method available for its preparation can of course be used.

1α,25(OH)$_2$D$_3$ can be prepared for example as described in Cohen, Z. et al, J. Org. Chemistry, 41, 2651-2652 (1976).

A preferred method consists in preparing the 1 keto-25(OH) previtamin D$_3$ directly from the 1α,25(OH)$_2$ previtamin D$_3$ by MnO$_2$ oxidation. 1α,25(OH)$_2$ pre D$_3$ can be prepared according to Semmler et al, Tetrahedron Letters, 40, 4147–4150 (1972) using the saponification of Barton et al, J.Chem,Soc,ChemComm,203 (1974).

Reduction of 1-keto25(OH) previtamin D$_3$ with $^3$H-NaBH$_4$ according to equation 1, supra, is carried out at $-25°$ to $+25°$ C., preferably $-10°$ to $+10°$ C., most preferably around 0° C., in a non-reducible inert polar organic solvent such as methanol, ethanol, a glycol, or other similar solvent.

Aqueous mixtures of the aforementioned solvents can also be used. The molar ratio of 1 keto-25(OH) previtamin D$_3$ to $^3$H-NaBH$_4$ is 1:10, preferably 1:5, most preferably 1:2, and the reaction is run for periods ranging between 10 minutes and 5 hours. The reaction can be readily followed by monitoring the disappearance of ultraviolet peaks at 288 nm and 238 nm and the appearance of a peak at 260 nm, and it can be stopped when the spectral changes have come to an end. After reaction, the excess NaBH$_4$ is destroyed by reaction with a ketone, such as acetone, by extracting the mixture between water and a water immiscible organic solvent such as ether, and finally combining the organic solvent layers, which contain a mixture of tritiated 1α,25(OH)$_2$ preD$_3$ and tritiated 1β,25(OH)$_2$ preD$_3$.

These two epimers are now separated by chromatography, preferably by adsorption chromatography or by gel permeation chromatography. Among the useful adsorption chromatography methods are high pressure liquid chromatography on a μPorasil ® column, chromatography on silicic acid, thin layer preparative chromatography, alumina or silica gel chromatography, reverse phase chromatography, and the like. Most preferred among these is high pressure liquid chromatography (hplc) because of the ease and rate of separation. A 5% isopropanol/hexane solution (3 ml/min) as eluent has been found especially useful for an hplc separation. Because of the high specific activity of the compounds and the possibility of contamination of the instruments, however, other methods can be routinely employed.

Among the useful gel permeation methodologies are Sephadex ® or Lipidex ®. Sephadex ® LH-20 is particularly preferred, using a chloroform:hexane (65:35 v/v) solution as eluent.

After tritiated $1\alpha,25(OH)_2$ preD$_3$ is separated from its undesired epimer $1\beta,25(OH)_2D_3$, the isolated, desired $1\alpha,25(OH)_2$ preD$_3$ is thermally equilibrated with its corresponding vitamin D$_3$ isomer, as shown in equation (2) supra. This reaction is also well known from the work of Paaren et al and Sheves et al, supra. The isomerization occurs efficiently (95%) at room temperature, albeit slowly. Therefore, and although the yields are somewhat lower, it is preferred to carry it out at somewhat more elevated temperatures such as 40°–100° C., most preferably 50°–80° C. for a period of time ranging from 2–8 hours, in inert solvents, such as alcohols. The reaction yields approximately a 4:1 mixture of the desired vitamin to the previtamin respectively. The thermal mixture can then be separated by chromatography, preferably hplc to obtain substantially pure or pure $[1\beta\text{-}^3H]1\alpha,25(OH)_2D_3$ (IV).

It will be readily apparent that with the availability of $[1\beta\text{-}^3H]1\alpha,25(OH)_2D_3$ of high specific radioactivity, it is possible to further study the sidechain cleavage metabolism of this vitamin. The invention also provides vitamin of specific activity which is high enough to be readily used in radioimmunoassays, competitive binding assays, tracer studies and the like. $[1\alpha\text{-}^3H]1\beta,25(OH)_2D_3$ which is also obtained by the process of the invention is useful for tracer studies in chromatographic identifications, or the like.

Having generally described this invention, the same will be further understood by reference to certain specific examples which are included herein for purposes of illustration only and are not intended to be limitative thereof.

EXAMPLE 1

Chemical Synthesis of $1\alpha$ and $1\beta,25$-Dihydroxyvitamins D$_3$

Activated manganese dioxide was prepared by adding, simultaneously, aqueous solutions of manganese sulfate monohydrate and sodium hydroxide to a hot aqueous solution of potassium permanganate with stirring during 1 hour. The brown precipitate was washed until free of potassium permanganate and then dried at 110° C. for 24 hours.

To 40 mg of $1\alpha,25\text{-}(OH)_2\text{-}D_3$ or 40 mg of $1\alpha,2\text{-}5(OH)_2$preD$_3$ in 30 ml of dry methylene chloride was added in increments, 200 mg of activated manganese dioxide, and the reaction mixture was stirred for 3 hours at room temperature when thin-layer chromatography (t.l.c.) (chlorofrom:ethyl acetate 1:9, v/v) indicated approximately 50% oxidation. The reaction mixture was dried under nitrogen and then applied to a glass column (2 cm × 17 cm) packed with Sephadex ® LH-20, slurried and developed in 7:3 v/v chloroform:n-hexane. Fractions (4.0 ml) were collected, and fractions 15–25, having the UV spectrum $\mu$ max (ether) 288,238 nm of 1-oxo-25-hydroxy-previtamin D$_3$, were combined to give 15 mg of product.

To a solution at 0° C. of 1-oxo-25-hydroxy-previtamin D$_3$ in 10 ml methanol and 100 $\mu$l distilled water was added 20 mg NaBH$_4$. The reduction was continued for 1 hour, when the UV spectrum showed the disappearance of the 288- and 238-nm peaks and the appearance of a 260-nm peak. The solution was distributed between ether and water, the aqueous layer was withdrawn and extracted with ether, the ether layers were combined and the procedure was repeated twice. The $1\beta,25$-dihydroxy-previtamin D$_3$ ($1\beta,25\text{-}(OH)_2$-preD$_3$) and $1\alpha,25$-dihydroxy-previtamin D$_3$ ($1\alpha,2\text{-}5(OH)_2$-preD$_3$) were isolated by high-pressure liquid chromatography (h.p.l.c.) (Waters Associates) on a $\mu$Porasil ® column (5% v/v isopropanol/hexane, 3 ml/min). Under these conditions, $1\beta,25\text{-}(OH)_2$-preD$_3$ (FIG. 1) is eluted much earlier ($t_r$ 14 min) than $1\alpha,2\text{-}5(OH)_2$-preD$_3$ ($t_r$ 28 min), $1\alpha,25\text{-}(OH)_2$-D$_3$ ($t_r$ 26 min), and $1\beta,25\text{-}(OH)_2$-D$_3$ ($t_r$ 24 min).

Thermal isomerization of $1\beta,25\text{-}(OH)_2$-previtamin D$_3$ (MeOH, 60° C., 3 hours) followed by purification by h.p.l.c. yielded $1\beta,25\text{-}(OH)_2$-D$_3$ ($\lambda_{max}$265 nm), $^1$H n.m.r. $\delta$0.54 and 1.00 (s, 13-Me, 25-Me$_2$), 4.10 (m, 3-H), 4.32 (m, 1-H), 5.00 ($\delta$, J 2.0 H$_2$, 19 (Z)-H), 5.28 ($\delta$, 1.4 HZ, 19 (E)-H), and 6.44 and 6.04 (AB$_q$, J 11.8 HZ, 6- and 7-H). Thermal isomerization of $1\alpha,25\text{-}(OH)_2$-pre D$_3$ (MeOH, 60° C., 3 hours) followed by h.p.l.c. yielded $1\alpha,25\text{-}(OH)_2$-D$_3$ ($\lambda_{max}$265), ($\lambda_{min}$228 nm)

EXAMPLE 2

Radiochemical Synthesis

In an analogous sequence to that of Example 1, 1-keto-25-hydroxy-previtamin D$_3$ (2.0 mg) was dissolved in 5 ml MeOH and reduced with 1.0 mg $^3$H-NaBH$_4$ (S.A. 80 Ci/mM, New England Nuclear) at 0° C. for 60 minutes. The excess $^3$H-NaBH$_4$ was reacted with acetone and dried in vacuo. The reaction mixture was dissolved in 1.0 ml 65:35 v/v CHCl$_3$:n-hexane and applied to a 1.5 × 30-cm glass column containing 15 g Sephadex ® LH-20 that was slurried in the same solvent. The products $^3$H-$1\beta,25\text{-}(OH)_2$-preD$_3$ and $^3$H-$1\alpha,25\text{-}(OH)_2$-preD$_3$ eluted between 70 and 100 ml and 150 and 200 ml, respectively. The isolated previtamin D$_3$ epimers were warmed at 60° C. for 6 hours in MeOH, which thermally isomerizes the previtamin D's to corresponding $1\beta,25\text{-}(OH)_2$-D$_3$ and $1\alpha,25\text{-}(OH)_2$-D$_3$ in an equilibrium ratio of approximately 1:4 preD:D.

Figure 2:
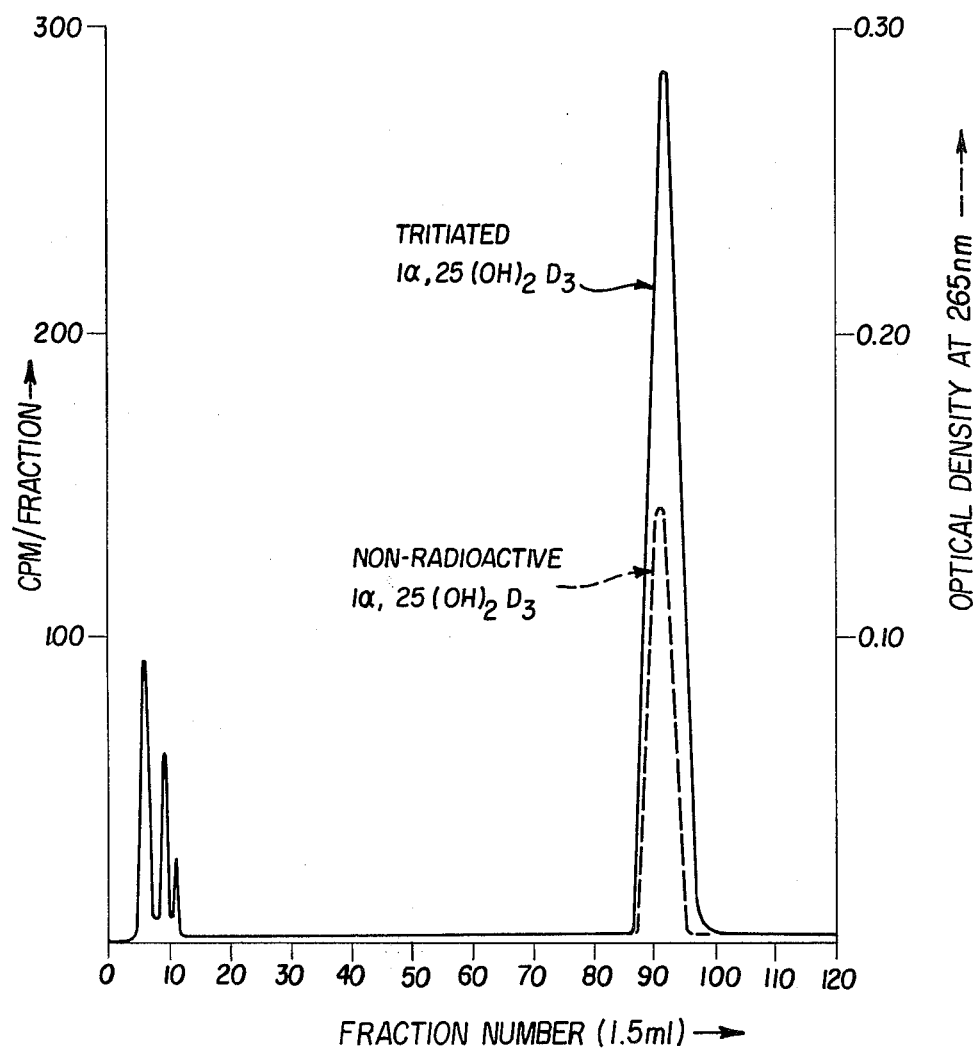
FIG. 2 is a high-pressure liquid chromatography profile of a mixture of radioactive [1β-$^3$H]1α,2-5(OH)$_2$D$_3$ and non-radioactive 1β,25(OH)$_2$D$_3$, according to Example 2.

The equilibrium reactions were chromatographed separately in h.p.l.c. as described in Example 1. The products $[1\alpha\text{-}^3H]\text{-}1\beta,25\text{-}(OH)_2\text{-}D_3$ and $[1\beta\text{-}^3H]\text{-}1\alpha,25\text{-}(OH)_2\text{-}D_3$ had identical ultraviolet absorption spectra ($\lambda_{max}$265 nm, $\lambda_{min}$228 nm), characteristic of the 5,6-cis triene chromophore. Identity and radioactive purity of $[1\beta\text{-}^3H]\text{-}1\alpha,25\text{-}(OH)_2\text{-}D_3$ was established by cochromatography with authentic crystalline $1\alpha,25\text{-}(OH)_2\text{-}D_3$. $[1\beta\text{-}^3H]1\alpha,25(OH)_2D_3$ eluted identically with crystalline $1\alpha,25\text{-}(OH)_2\text{-}D_3$ on h.p.l.c. (FIG. 2). Each product had a specific activity of about 9 Ci/mmol.

Bioassays

Weaning male rats (Holtzman Co., Madison, Wisconsin) were fed a vitamin D-deficient diet adequate in calcium and phosphorus for two weeks, and were then switched to a vitamin D-deficient low-calcium (0.02%) diet for an additional two weeks. Groups of six rats received either 0.25 $\mu$g of standard $1\alpha,25\text{-}(OH)_2\text{-}D_3$, or 10 μg 1β,25-(OH)$_2$-D$_3$ intrajugularly in 50 μl 95% ETOH, while a control group received only the vehicle. Twenty-four hours after administration, the animals were decapitated and their duodena and blood collected. Intestinal calcium transport activity was measured by the everted gut sac technique, Schachter, D. et al., Amer. J. of Physiol. 200, 1263–1271 (1961) and bone calcium mobilization was determined based upon serum calcium measurements, Tanaka, Y. et al., Arch. Bioch. Biophys. 146, 574 (1971).

0.25 μg of 1α,25(OH)$_2$D$_3$ elicited intestinal calcium transport and bone calcium transport and bone calcium mobilization responses. 1β,25(OH)$_2$D$_3$ at a dose of 10 μg was unable to stimulate either intestinal calcium transport or bone calcium mobilization.

Having now fully described this invention, it will be apparent to one of ordinary skill in the art that many changes and modifications can be made thereto without departing from the spirit or scope of the invention set forth herein.

What is claimed as new and desired to be secured by Letters Patent of the United States is:

1. [1β-$^3$H]1α,25-dihydroxyvitamin D$_3$, having a specific activity of 1–20 Ci/mM.

2. The vitamin of claim 1 which has a specific activity of 5–20 Ci/mM.

3. A method of preparing [1β-$^3$H]1α,25-dihydroxyvitamin of claim 1 which comprises:
   reducing 1-keto-25(OH)previtamin D$_3$ with $^3$H-NaBH$_4$ thereby obtaining a mixture of [1β-$^3$H]1α,25 dihydroxy previtamin D$_3$ and [1α-$^3$H]1β,25-dihydroxyprevitamin D$_3$ epimers;
   separating said [1β-$^3$H]1α epimer from said [1α-$^3$H]1β epimer of dihydroxyprevitamin D$_3$ by chromatography;
   thermally equilibrating said separated [1β-$^3$H]1α,25-dihydroxyprevitamin D$_3$ with its [1β-$^3$H]-1α,25 dihydroxyvitamin D$_3$ isomer.

4. The method of claim 3 which further comprises separating said [1β-$^3$H]1α,25 dihydroxprevitamin D$_3$ from said [1β-$^3$H]1α,25 dihydroxyvitamin D$_3$.

5. The method of any of claims 3 or 4 wherein said $^3$H-NaBH$_4$ has a specific activity of ≧60 Ci/mM.

6. The method of claim 3 wherein said 1-keto 25(OH) previtamin D$_3$ is prepared from 1α,25 (OH)$_2$ previtamin D$_3$.

7. The method of claim 3 wherein said chromatography is adsorption chromatography.

8. The method of claim 7 wherein said adsorption chromatography is high pressure liquid adsorption chromatography.

9. The method of claim 3 wherein said chromatography is gel permeation chromatography.

* * * * *